(12) United States Patent
Sah et al.

(10) Patent No.: US 6,475,144 B1
(45) Date of Patent: Nov. 5, 2002

(54) NON-CONTACT METHOD FOR MEASURING AMOUNT OF SKIN SEBUM OR OIL IN REAL TIME USING FIBER OPTIC PROBE

(75) Inventors: Archana K Sah, Quincy, MA (US); Leonard Van Gorkom, Englewood, NJ (US); Zhenhe Zhu, deceased, late of Peekskill, NY (US), by Xi Yuan Zhu, legal representative; Thomas Hancewicz, Ringwood, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/884,395

(22) Filed: Jun. 19, 2001

(51) Int. Cl.$^7$ .................................................. A61B 5/00
(52) U.S. Cl. ...................................... 600/306; 600/310
(58) Field of Search ................................ 600/306, 310, 600/473, 476, 478

(56) References Cited

U.S. PATENT DOCUMENTS

| | | | |
|---|---|---|---|
| 4,224,950 A | | 9/1980 | Bore et al. |
| 4,313,393 A | | 2/1982 | Barbuscio et al. |
| 4,423,736 A | * | 1/1984 | DeWitt et al. ............... 600/306 |
| 4,480,921 A | * | 11/1984 | Leveque et al. ............ 356/434 |
| 4,846,184 A | * | 7/1989 | Comment et al. ........... 600/306 |
| 5,094,248 A | | 3/1992 | Kawam |

FOREIGN PATENT DOCUMENTS

| | | |
|---|---|---|
| JP | 02220630 | 9/1990 |
| JP | 05060686 | 3/1993 |
| JP | 09292214 | 11/1997 |
| WO | 96/25884 | 8/1996 |

* cited by examiner

*Primary Examiner*—Stephen M. Hepperle
(74) *Attorney, Agent, or Firm*—Ronald A. Koatz

(57) ABSTRACT

The invention provides a non-contact process for measuring amount of sebum or oil on skin or other substrate. Process is preferably done in vivo because of ability to measure formation of sebum/oil on skin in real time.

8 Claims, 7 Drawing Sheets

NON-CONTACT METHOD FOR MEASURING AMOUNT OF SKIN SEBUM OR OIL IN REAL TIME USING FIBER OPTIC PROBE

FIELD OF THE INVENTION

The present invention relates to non-contact methods for measuring quantity of sebum or oil on skin or other substrates. While measurement can be done in vivo or ex vivo, the technique is preferred for use in vivo because of the ability to measure formation of oil on the skin in real time.

BACKGROUND OF THE INVENTION

Methods of analyzing the quantity of sebum or oil produced using so-called contact techniques are known. Generally such contact methods mean that the measurement involves contact with the area where the sebum/oil is being measured. Since the sebum or oil is generally sampled and then measured, it is difficult or impossible to monitor changes in real time, i.e., as they are occurring. For example, "In-vivo infrared analysis of the recovery of sebaceous lipids after dilapidation", J. Invest. Dermatology, 112(4), 779 (1999), N. Kollias et al. describe an ATR-FTIR method for sebum detection using a fiber optic probe attachment. This is a contact method involving collection and transfer of sebum onto an ATR (attenuated total internal reflection device) crystal. Other contact methods include use of sebutape, use of a sebumeter and lipid extraction.

JP 09292214 (assigned to Sekisui Chemical) discloses a non-contact ultrasound method for measuring skin sebum. Here however, the ultrasound measures only the thickness of the fat layer, not actual amounts of sebum produced.

Other non-contact methods are also disclosed in the following references.

In JP 05060686, sebum is collected from the surface using a plate and then an IR spectrum is obtained using ATR device.

In JP 02220630, sebum quantity is measured using IR lights to detect reflected light from sebum collecting surface.

In U.S. Pat. No. 5,094,248 to Kawam, sebum is collected onto a hydrophilic open celled microporous polymeric film by patching to skin, and the amount of sebum collected is measured against a selected background by optical methods.

In U.S. Pat. No. 4,224,950 to Bore et al., sebum is collected onto a frosted glass plate and quantified using optional methods.

In U.S. Pat. No. 4,313,393 to Barbuscio et al., sebum is collected using an oil absorbent material, and the amount collected is quantified using a dye.

In WO 96/25884 to (assigned to Courage & Khazaka), sebum secretion on skin is measured using a microporous water repellent, sebum absorbing opaque foil which absorbs sebum and changes in transparency.

None of these methods are true "non-contact" methods and, therefore, they do-not allow monitoring sebum levels in vivo in real time.

Unexpectedly, applicants have discovered that it is possible to measure quantity of sebum or oil in vivo using non-contact technique. This also allows real time measurement.

BRIEF DESCRIPTION OF INVENTION

The present invention relates to a non-contact (non-invasive) method for measuring quantity of sebum or oil on skin substrate. Because the measurements are truly non-contact, they can be made in real time on the same sites for any desired length of time.

The present invention discloses one specific embodiment for non-contact measurement. A second embodiment is disclosed in a separate application filed on same day as the subject application.

In the present invention, the amount of sebum or oil is detected by diffuse reflectance, in the near-IR to mid-IR range (400 $cm^{-1}$ to 10,000 $cm^{-1}$). The measurement is made by choosing a desired spot (typically 0.1 to 10 cm) on the subject's body (e.g., forehead); positioning a fiber optic probe on the spot about 0.1 to 40 cm away from the spot reflecting infrared (IR) light (typically of wavenumber 400 to 10,000 $cm^{-1}$) against the spot; and measuring the IR reflectance spectra in the wavenumber range. Analysis and quantification is achieved via chemometrics as described in the examples (i.e., using C-H and triglyceride overtone absorbance near defined wavenumber).. In an alternative embodiment, the method can be used for near infrared (NIR) imaging to measure oil/sebum on the desired substrate in specified wavenumber range.

More specifically, the invention comprises a non-contact process or method for measuring sebum or oil from skin or other substrate comprising:

(1) choosing a desired spot, typically 0.1–10 cm, preferably 0.2–9 cm, more preferably 0.2–3 cm on the body of a subject;

(2) positioning a fiber optic probe on the spot about 0.1–40 cm, preferably 0.1 to 2 cm away from the spot;

(3) reflecting infrared light in the 400 to 10,000 $cm^{-1}$ wavenumber range against said spot; and (4) measuring an infrared reflectance spectra in said wavenumber range (e.g., using info gathered from the absorbance of C-H overtone combination bands in the 5000–7000 $cm^{-1}$ range).

As noted, step 4 measurement may alternatively comprise near IR imaging to measure oil/sebum in specified wavenumber range.

DETAILED DESCRIPTION OF THE INVENTION

Figure 1:
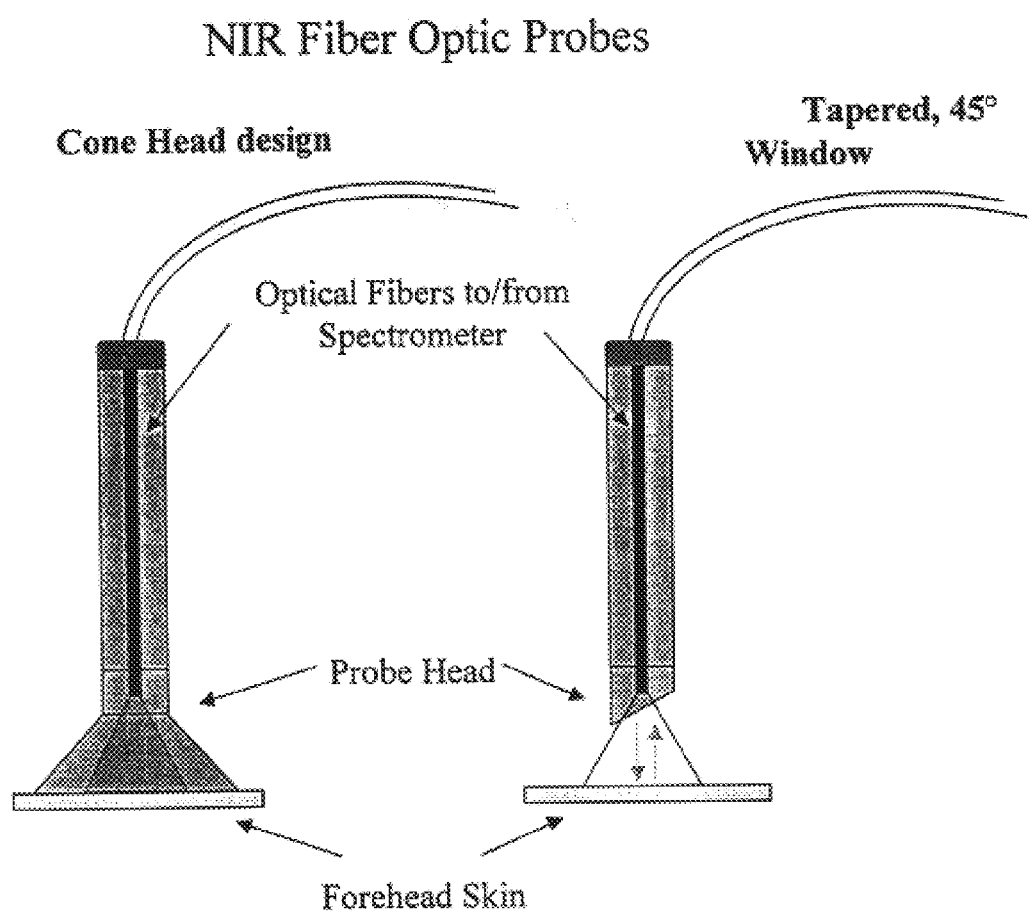
FIG. 1 is figure of fiber probes having either tapered probe (right) or preferred cone probe (left).

The present invention relates to a non-contact method for measuring quantity of sebum or oil on skin or other substrate, preferably in-vivo. The measurement could be done ex-vivo but the advantage of "real time" measurement would be lost. In alternative embodiment, the method can be used for NIR imaging to measure oil/sebum on the desired substrate in the specified wavenumber range.

Specifically, the invention provides a method for measuring sebum or oil from skin or other substrate like fabrics, hard surfaces etc. in vivo in real time. In general it is preferred although not required, that the substrate has diffused reflectance properties at the desired wavelengths. The process/method comprises:

(1) choosing a desired spot, typically 0.1–10 cm, preferably 0.2–3 cm diameter, on body of subject to be measured;

(2) positioning a fiber optic probe on said spot; preferably the probe has a collar, more preferably a conical/funnel shaped probe head that controls the angle of the light incident on the substrate and the distance (e.g., 0.1–40 cm, preferably 0.1–2 cm from spot) of substrate from source is preferred as noted;

(3) reflecting infrared rays of defined wavenumber range (e.g., 700 cm$^{-1}$ to 10,000 cm$^{-1}$) against said spot; and (4) measuring sebum, oil or substrate quantity based on infrared reflectance spectra in wavenumber range or, alternatively, based on near IR imaging.

Each of the process steps is discussed in more detail below and in the examples.

The first step in the non-contact infra-red (IR) method of measuring sebum or oil on skin or other substrate according to the subject invention is to choose a subject and choose a desired spot on the subject suitable for IR measurement techniques of sebum/oil release.

A preferred location for sebum production and measurement is the forehead. A typical test site is about 3 cm in diameter, although this may vary as widely, for example, from 0.1 to 10 cm in diameter. Looking at sites on the right side, left side or center of forehead, typically the center site is preferred as this would typically yield most amount of sebum.

In the second step of the process, the fiber optic probe (e.g., a spectrometer such as Nicolet Magna 550® FTIR spectrometer equipped with an NIR spectral probe) is positioned against (but not in contact with) the desired spot. Typically the probe head is positioned 0.1 cm to 40 cm, preferably 0.1 cm to 3 cm from the chosen spot.

Preferably, the probe has a collar. In a preferred embodiment, the head of the probe is designed in a funnel like or conical shape in order to reduce spectral variability and enable easier sampling procedure.

In the third step of the invention, the infrared rays of defined wavenumber are reflected from the probe to the measurement site.

Typically, an NIR probe is used to collect a spectrum from the site (e.g., forehead site). Spectrum is collected from 700 to 10,000 cm$^{-1}$ range, preferably 4200 to 7,000 cm$^{-1}$ range, more preferably in the 5,000 to 6,000 cm$^{-1}$ range.

Finally, in the fourth step, measurement of sebum or oil is gathered from absorbance of C-H and triglycerides overtone and combination bands in the spectral range as earlier specified. Alternatively, measurement may be based on near IR imaging.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES & METHODOLOGY

Analysis of Sebum Spectra

Pre-Processing Data

Raw data needs to be pre-processed prior to further analysis. The typical reasons for doing this is to eliminate large sources of variation that are unrelated to the chemical information being extracted from the data. Common sources of such variations, particularly with NIR reflectance data, are baseline offset variation where the spectrum-to-spectrum baseline moves up and down in a random fashion. This is related to inconsistency in sampling and should be corrected. Also of concern is the random variation in spectral scaling which often occurs in reflectance spectroscopy. This too is caused by inconsistent sampling, primarily due to small changes in the angle of light collection. These are the two problems that plague NIR reflectance spectroscopy and should be corrected.

Multivariate Curve Resolution

Multivariate Curve Resolution (MCR) is a least-squares method that tries to minimize the residuals between the original data and the optimized data. The first step in MCR is to generate initial estimates for the least-squares optimization process. This can be done using any of a number of techniques, but the standard method is to use results from principal factor analysis (PFA or PCA). PFA separates the original data into the product of a score matrix (related to the relative concentration profiles), and a factor matrix (related to the pure spectra). The factors and scores are extracted according to the major sources of variance in the data. The number of significant sources of variation related directly to the chemical components of interest is called the chemical rank of the data matrix and is typically the first several factors in the PFA results. The rest of the factors are unimportant to the resolution of the data and can be ignored.

The number of significant factors is ideally equal to the number of substances contributing to the variation in the mixture spectra. In practice however it is more difficult to determine the number of chemical components than it would first appear. This is due primarily, to disturbances introduced by drifting baselines, non-linear detector response, spectrometer noise, and sampling variability. Furthermore the variation introduced by components of low concentration, or by those exhibiting very similar spectra, is very small, and therefore difficult to detect, especially when several similar compounds co-exist. Robust statistics are generated to aid in determining the exact number of significant chemical factors.

In the final step the data matrix is resolved into pure spectra and concentration profiles by alternating regression also called alternating least-squares regression (ALS). Alternating regression is a procedure by which spectra and concentration profiles are refined in an iterative process until the pure variables emerge.

At the end of the MCR analysis, the spectrum of the pure substances such as sebum, water, and skin, and the concentration profiles of each over time are obtained directly from the solution.

Partial Least-Squares Modeling

Partial Least-Squares Modeling (PLS) functionally is the same mathematical operation as MCR with a few differences. Whereas MCR uses a self-modeling approach to a minimized least-squares solution, PLS uses a hard-modeling "brut force" approach to force the best solution based on the calibration data. Therefore, PLS will only give good results for components captured in the calibration model. States another way, it will only find a component it thinks is in the data. Another difference with MCR is that PLS does not perform the initial estimates and least-squares optimization in separate steps; it performs both operations in a single step. It effectively maximized variance (as in PFA) as it correlates to component concentration in the calibration data. It does this simultaneously and so produces the best comprise between capturing variance in the x-block data (raw data) and correlation in the y-block data (calibration information).

Materials

All near infrared (NIR) spectral measurements are taken on a Nicolet Magna 550 FTIR spectrometer equipped with a NIR spectral probe (Nicolet Instruments Corp.). The probe head was further redesigned into a funnel shape (see FIG. 1) to reduce spectral variability and enable easier sampling procedure.

Methods

Figure 2:
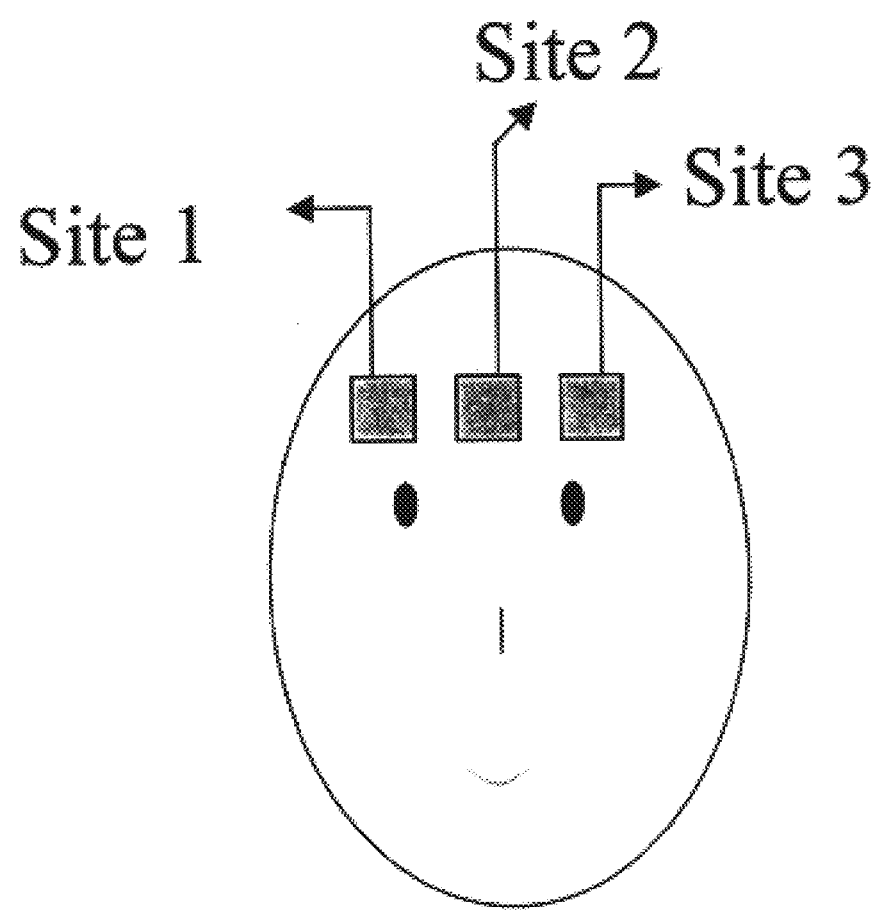
FIG. 2 shows head with possible test sites. Site 2 is preferred.

A NIR probe was used to collect a spectrum from human forehead sites in the 9915–4285 $cm^{-1}$ range. Sebum information was gathered form the C-H and triglycerides overtone absorbance near 5650 and 5785 $cm^{-1}$. Three test sites were used on foreheads (see FIG. 2). Each test site measured 3 cm in diameter. Alcoholic solution of artificial sebum was applied uniformly on each test site at 4.5 ul/$cm^2$ with a positive displacement pipette. The alcohol was allowed to evaporate for 1–2 minutes, thereafter triplicate readings were taken at each site, 64 co-added scans.

Examples—Study A & B

Two initial studies were conducted with a probe head which did not have the funnel design.

Study A: The first study investigated the regreasing kinetics of sebum level at five sites on the forehead over a period of six hours.

Study B: The second study, a calibration feasibility study, was conducted dosing known amounts of artificial sebum on pig sin with the NIR probe using the previous probe head design.

Results and Discussion

Figure 3:
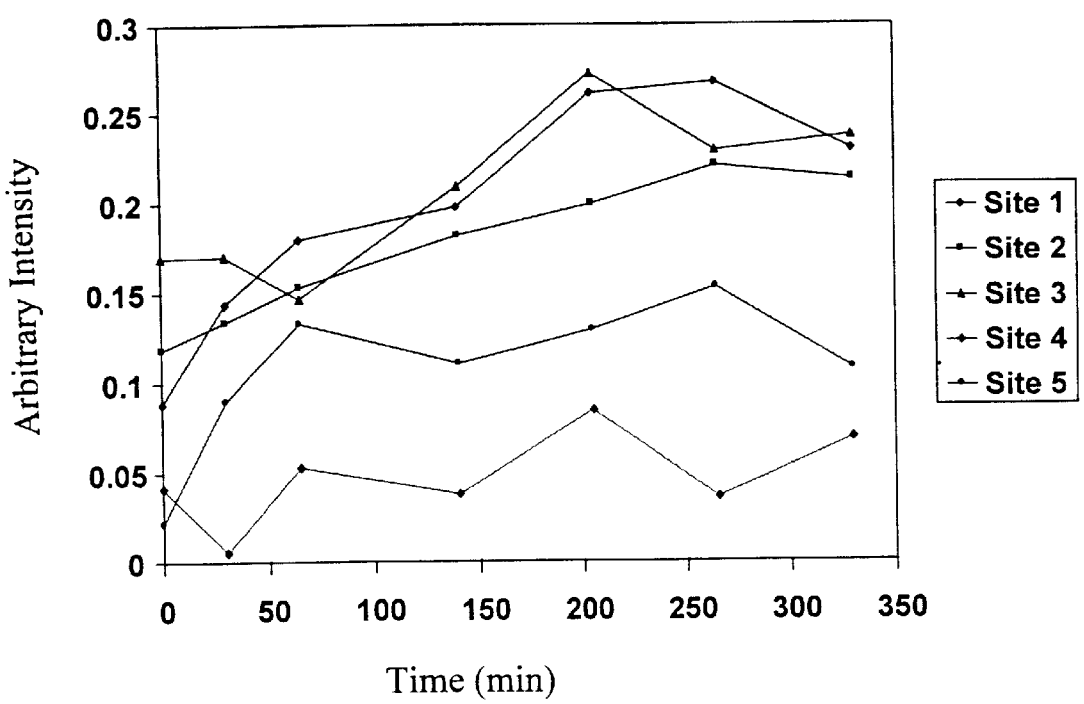
FIG. 3 shows general trend of increasing sebum with time.

Results from study A, investigating sebum regreasing kinetics, is reported in FIG. 3. The figure shows an increase in sebum on human foreheads over the six hours period with high amount of variability in the amounts of sebum on the five sites. However, the results were not reproducible because of the very high variability in the spectral data. Even so, the general trend of increasing sebum with time can be observed.

Figure 4:
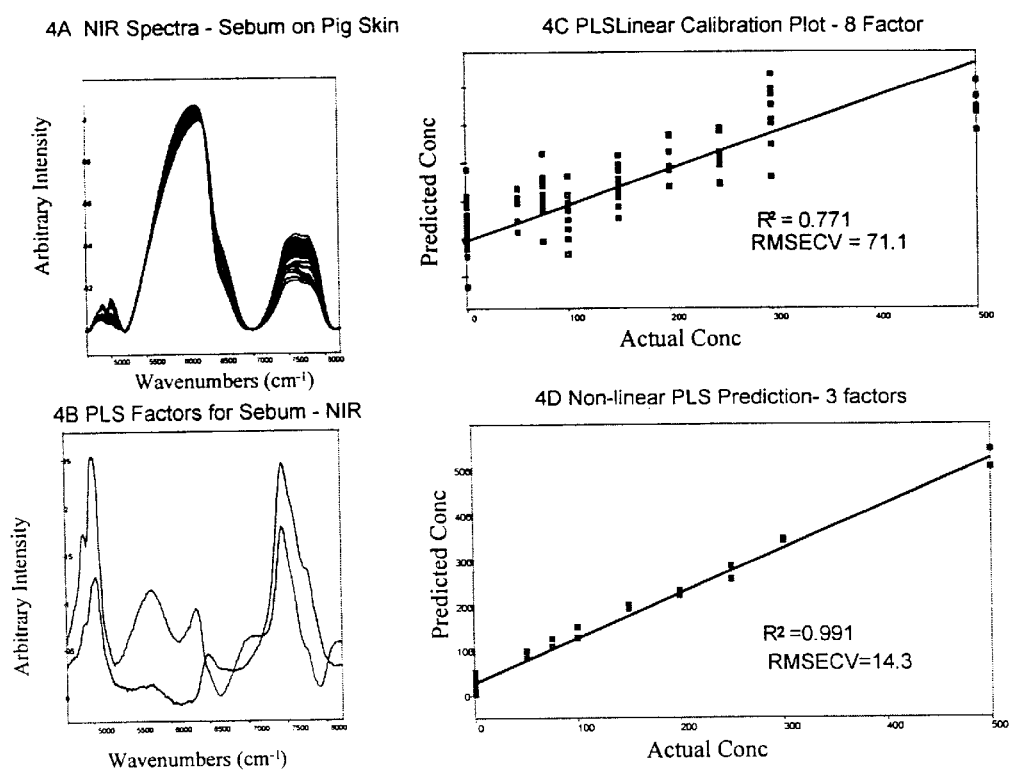
FIG. 4 shows calibration on pig skin using old probe designed as discussed herein.

Results form Study B, calibration on pig skin with the old probe design, are shown in FIG. 4. FIG. 4B and 4A show the original NIR spectra after preprocessing, and the PLS extracted components for sebum, respectively. It requires more than one profile to model sebum concentration due to a slightly non-linear spectral response with increased sebum concentration. The PLS prediction results are shown in FIGS. 4C and 4D for an 8-factor linear PLS calibration model and a 3-factor non-linear PLS model respectively. This clearly shows that a non-linear trend exists in the calibration data and is most accurately modeled using a non-linear algorithm. A repeat of this experiment on human skin rather than pig skin showed a much larger error of prediction owing to the much larger variation due to spectral sampling. This reproducibility issue can be addressed through a better probe design, e.g., funnel probe.

Examples—Study C & D

Study C: A regreasing kinetic study was conducted wherein the forehead was washed with Lux soap lather for 1 minute followed by a 30 seconds rinse with tap water. After a 10 minute equilibration period for the excess water to evaporate, three circular sites with 3 cm diameter were marked on the forehead using a surgical skin marker. Thereafter triplicate sebum readings were taken on each site on the forehead at time points 0, 0.5, 1, 1.5, 2, 2.5, 3, 3.5, 4, 5 and 6 hours. The spectra were collected using the Magna 500 Spectrometer using the redesigned NIR probe. Each spectrum was collected with 16 $cm^{-1}$ resolution and 62 co-added scans.

Study D: A calibration study was conducted dosing 4.1 ul/$cm^2$ of artificial sebum at concentrations of 100, 500 and 1000 ug/$cm^2$ on human forehead at the middle site using a positive displacement pipette. After the alcohol evaporated, the triplicate spectra was collected for each of the three concentrations of artificial sebum.

Figure 5:
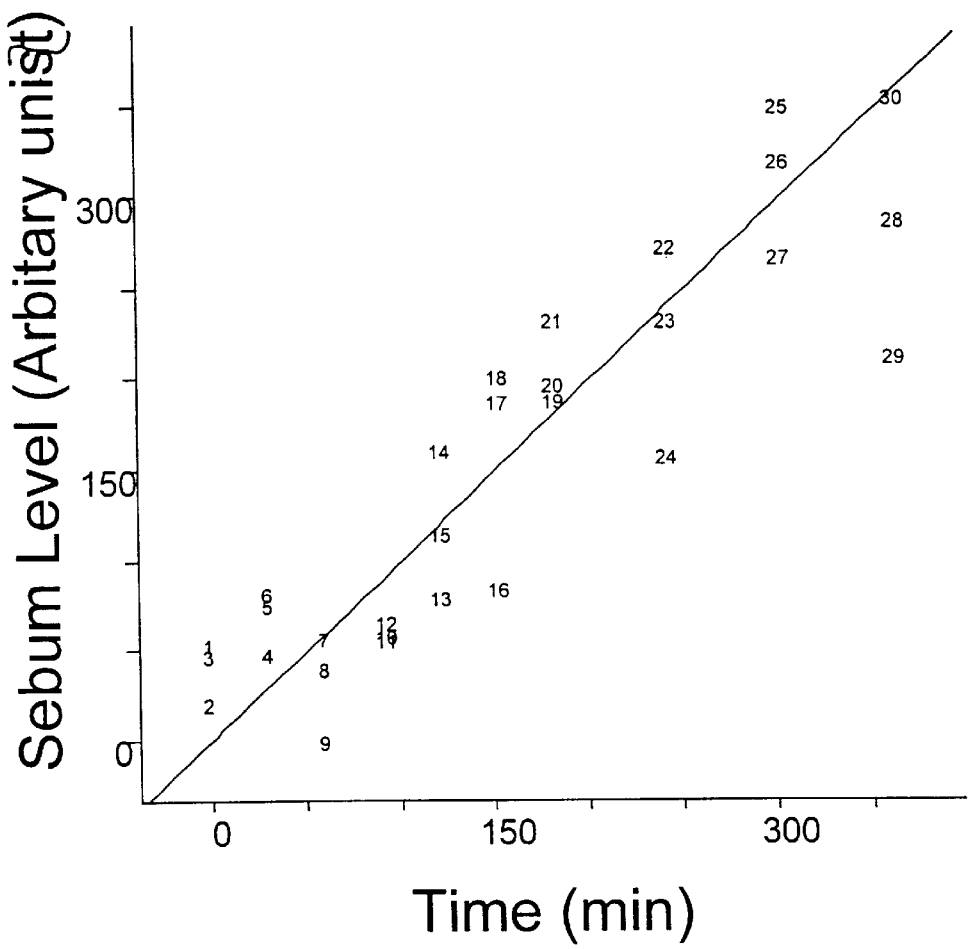
FIG. 5 shows results from re-greasing kinetics study on human foreheads with new probe head. There is clear correlation between NIR sebum response and time.

Results for the regreasing kinetics study on human foreheads with the new probe head (Study C) is shown in FIG. 5. The plot shows a correlation between NIR sebum response versus time.

Figure 6:
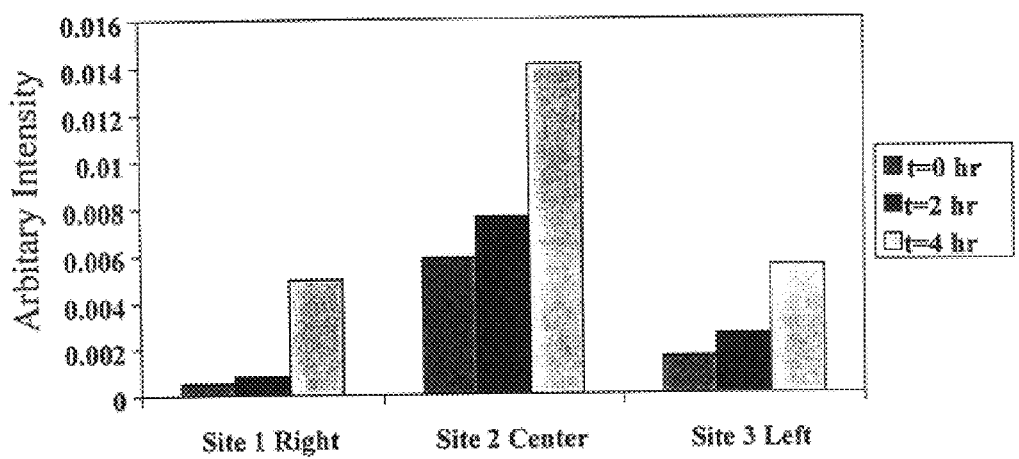
FIG. 6 shows that maximum amount of sebum on forehead is collected on central forehead site.
Figure 7:
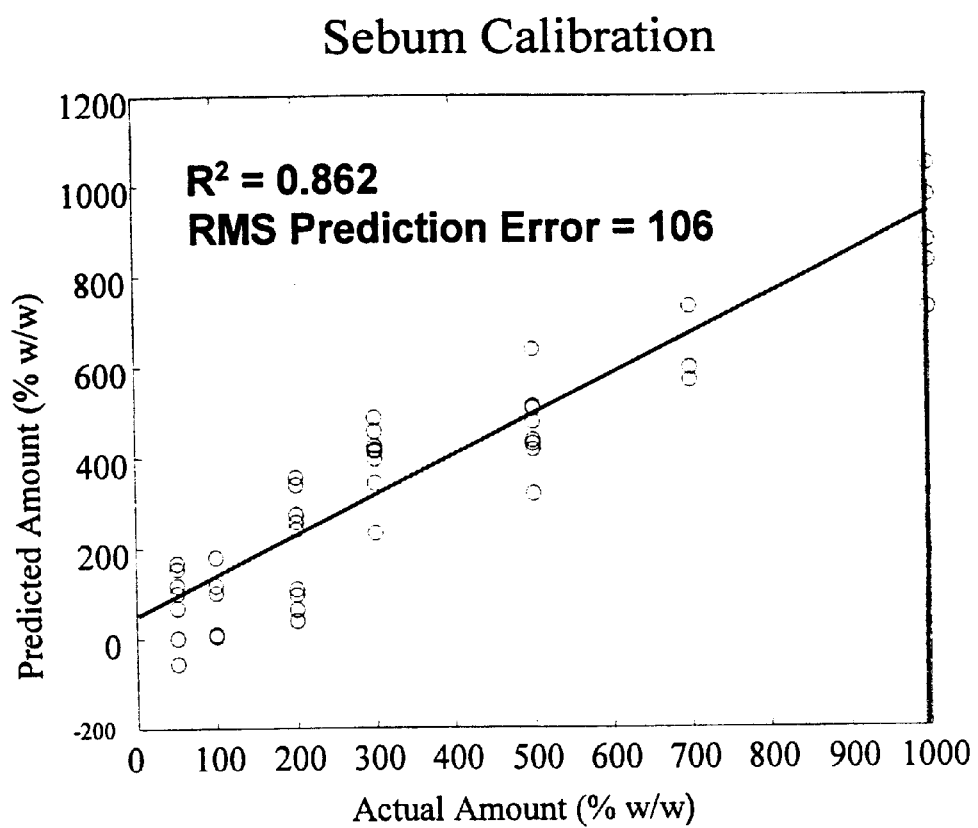
FIG. 7 shows sebum calibration.

The plot uses a $3^{rd}$ order polynomial PLS regression model for 2–4 factors. A good correlation was observed between the actual and the predicted sebum response ($R^2$= 0.811). Investigating the site-to-site variability within three sites on the forehead showed the maximum amount of sebum to be along the central site (FIG. 6). This was quite consistent with published literature of that being the highest along the central C-fold.

Results of the calibration study (Study D) conducted to establish a calibration algorithm to measure sebum levels on human foreheads indicate a good correlation factor.

This is generally considered quite remarkable given that the amounts of spectral variations in sebum as well as that being contributed by the sampling technique. The calibration study shows that it is possible to quantify sebum levels on human foreheads in vivo into three broad categories of low, medium and high sebum levels using the current algorithm.

What is claimed is:

1. A non-contact process or method for measuring sebum or oil on skin or other substrates comprising:
    (a) choosing a desired spot on the body of a subject;
    (b) positioning a fiber optic probe on the spot;
    (c) reflecting infrared light in the 400 to 10,000 $cm^{-1}$ wavenumber range against said spot; and
    (d) measuring an infrared reflectance spectrum in said wavenumber range.

2. A process according to claim 1, wherein substrate comprises hair or fabric.

3. A process according to claim 1, wherein said desired spot is on the forehead.

4. A process according to claim 1, wherein said spot is 0.1 to 10 cm in diameter.

5. A process according to claim 1, wherein said probe is positioned 0.1 to 40 cm from said desired spot.

6. A process according to claim 1, wherein said probe is funnel or conical shaped.

7. A process according to claim 1, wherein measurement is obtained using information gathered from absorbance of C—H overtone and combination bands in the 500–7000 $cm^{-1}$ range.

8. A non-contact process or method for measuring sebum or oil on skin or other substrates comprising:
    (a) choosing a desired spot on the body of a subject;
    (b) positioning an imaging device on the spot;
    (c) reflecting infrared lights in the 400 to 10,000 $cm^{-1}$ wavenumber range against said spot; and
    (d) measuring by imaging in said wavenumber range.

* * * * *